US011415455B2

(12) United States Patent
Rogers

(10) Patent No.: US 11,415,455 B2
(45) Date of Patent: Aug. 16, 2022

(54) GAS SENSOR WITH AN RF RESONATOR

(71) Applicant: The Boeing Company, Chicago, IL (US)

(72) Inventor: John E. Rogers, Owens Cross Roads, AL (US)

(73) Assignee: The Boeing Company, Chicago, IL (US)

( * ) Notice: Subject to any disclaimer, the term of this patent is extended or adjusted under 35 U.S.C. 154(b) by 79 days.

(21) Appl. No.: 16/874,673

(22) Filed: May 14, 2020

(65) Prior Publication Data

US 2021/0356301 A1 Nov. 18, 2021

(51) Int. Cl.
| | |
|---|---|
| *G01H 3/00* | (2006.01) |
| *G01D 11/24* | (2006.01) |
| *G01N 27/18* | (2006.01) |
| *H01P 7/06* | (2006.01) |
| *G01N 33/00* | (2006.01) |
| *G01H 13/00* | (2006.01) |

(52) U.S. Cl.
CPC ............ *G01H 3/00* (2013.01); *G01D 11/245* (2013.01); *G01H 13/00* (2013.01); *G01N 27/18* (2013.01); *G01N 33/0027* (2013.01); *H01P 7/06* (2013.01)

(58) Field of Classification Search
CPC .............. G01N 27/18; G01N 33/0009; G01N 33/0027; G01H 3/00; G01H 13/00; H01P 7/06; H01P 7/065; G01D 11/245
See application file for complete search history.

(56) References Cited

U.S. PATENT DOCUMENTS

| 6,019,505 A * | 2/2000 | Bonne ................. G01N 27/18 374/40 |
| 6,208,227 B1 * | 3/2001 | Remillard ............. H01P 7/06 333/219 |
| 2003/0089157 A1 * | 5/2003 | White ................... G01C 19/56 73/1.77 |
| 2014/0076024 A1 * | 3/2014 | Duraffourg ........... G01N 25/18 73/23.4 |

OTHER PUBLICATIONS

Fonseca, M. A., et al., "Flexible wireless passive pressure sensors for biomedical applications," Solid-State Sensors, Actuators, and Microsystems Workshop, Hilton Head Island 2006, Jun. 2006.
Hallil, H., et al., "Feasibility of wireless gas detection with an FMCW RADAR interrogation of passive RF gas sensor," IEEE Sensors, Nov. 2010.

(Continued)

*Primary Examiner* — Benjamin R Schmitt
(74) *Attorney, Agent, or Firm* — Haynes and Boone, LLP

(57) ABSTRACT

A gas sensor for detecting a gas in an environment is disclosed. The gas sensor comprises a housing having a cavity and a vent hole within the housing and a distributed element resonator within the cavity. The cavity includes a bottom surface and a top surface, and the housing is configured to receive the gas from the environment into the cavity through the vent hole. The distributed element resonator has an input terminal configured to receive a radio frequency input signal and an output terminal configured to produce an output signal.

20 Claims, 13 Drawing Sheets

(56) References Cited

OTHER PUBLICATIONS

Bouaziz, S., et al., "Novel microfluidic structures for wireless passive temperature telemetry medical systems using radar interrogation techniques in Ka-band," IEEE Antennas and Wireless Propagation Letters, Jan. 2013.

Mariotti, C., et al., "Development of low cost, wireless, inkjet printed microfluidic RF systems and devices for sensing or tunable electronics," IEEE Sensors Journal, Jun. 2015.

Rogers, J.E., et al., "A passive wireless microelectromechanical pressure sensor for harsh environments," Journal of Microelectromechanical Systems, Feb. 2018.

* cited by examiner

GAS SENSOR WITH AN RF RESONATOR

BACKGROUND

1. Technical Field

The field of the present disclosure relates generally to sensors, and more specifically, to gas sensors.

2. Prior Art

At present, there is a need in aerospace environments for detecting gases (e.g., combustible, hydrocarbon, carbon dioxide, volatile organic compounds, etc.) on-board aircraft (e.g., cockpit, cabin, wings, etc.) as well as on the factory floor. Generally, gas sensors are devices that are configured to sense gases, some of which are non-detectable to humans.

The types of existing gas sensors include semiconductors, electro-optical, electrochemical, and capacitive devices. Unfortunately, these types of sensors utilize electronics for power and signal conditioning that are either internal or local to the gas sensor. These electronics are typically based on semiconductor materials, which are well-known to degrade or fail with elevated temperature. As such, there is a need for an improved gas sensor that does not have internal or local electronics and is constructed of high temperature compatible materials.

SUMMARY

Disclosed is a gas sensor for detecting a gas in an environment. The gas sensor comprises a housing having a cavity and a vent hole within the housing and a distributed element resonator within the cavity. The cavity includes a bottom surface and a top surface, and the housing is configured to receive the gas from the environment into the cavity through the vent hole. The distributed element resonator has an input terminal configured to receive a radio frequency input signal and an output terminal configured to produce an output signal.

In an example of operation, the gas sensor performs a method that comprises receiving the gas from the environment into the cavity within the housing and exciting the distributed element resonator within the cavity with the radio frequency input signal. The method also comprises measuring the output signal from the output terminal that is in signal communication with the distributed element resonator.

The gas sensor may be fabricated by a method utilizing a deposition process. The method comprises etching the cavity in a first substrate having a top surface and a bottom surface, where the cavity is etched on the bottom surface, etching the vent hole through the bottom surface and top surface of the first substrate, and depositing a first metallic layer on a second substrate. The second substrate has a top surface and a bottom surface, and the first metallic layer is deposited on the top surface of the second substrate. The method also comprises etching the distributed element resonator on the first metallic layer, depositing a second metallic layer on the bottom surface of the second substrate to define a ground plane, and bonding the bottom surface of the first substrate to the top surface of the second substrate.

Other devices, apparatuses, systems, methods, features, and advantages of the invention will be or will become apparent to one with skill in the art upon examination of the following figures and detailed description. It is intended that all such additional devices, apparatuses, systems, methods, features, and advantages be included within this description, be within the scope of the invention, and be protected by the accompanying claims.

BRIEF DESCRIPTION OF THE FIGURES

The invention may be better understood by referring to the following figures. The components in the figures are not necessarily to scale, emphasis instead being placed upon illustrating the principles of the invention. In the figures, like reference numerals designate corresponding parts throughout the different views.

DETAILED DESCRIPTION

A gas sensor for detecting a gas in an environment is disclosed. The gas sensor comprises a housing having a cavity and a vent hole within the housing and a distributed element resonator within the cavity. The cavity includes a bottom surface and a top surface, and the housing is configured to receive the gas from the environment into the cavity through the vent hole. The distributed element resonator has an input terminal configured to receive a radio frequency input signal and an output terminal configured to produce an output signal.

In an example of operation, the gas sensor performs a method that comprises receiving the gas from the environment into the cavity within the housing and exciting the distributed element resonator within the cavity with the radio frequency input signal. The method also comprises measuring the output signal from the output terminal that is in signal communication with the distributed element resonator.

The gas sensor may be fabricated by a method utilizing a deposition process. The method comprises etching the cavity in a first substrate having a top surface and a bottom surface, where the cavity is etched on the bottom surface, etching the vent hole through the bottom surface and top surface of the first substrate, and depositing a first metallic layer on a second substrate. The second substrate has a top surface and a bottom surface, and the first metallic layer is deposited on the top surface of the second substrate. The method also comprises etching the distributed element resonator on the first metallic layer, depositing a second metallic layer on the bottom surface of the second substrate to define a ground plane, and bonding the bottom surface of the first substrate to the top surface of the second substrate.

Figure 1:
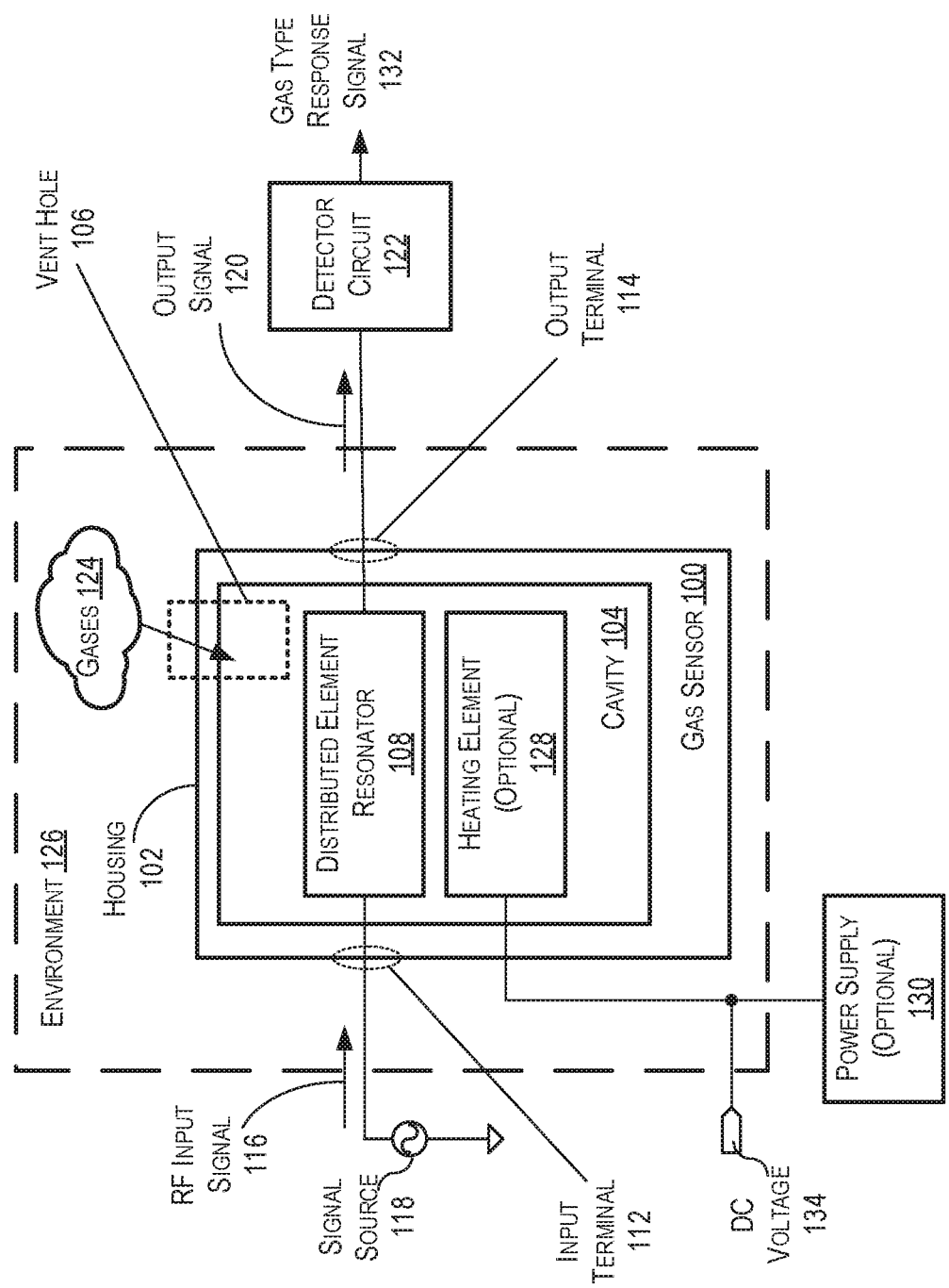
FIG. 1 is a system block diagram of an example of an implementation of a gas sensor in accordance with the present disclosure.

Turning to FIG. 1, a system block diagram of an example of an implementation of a gas sensor 100 is shown in accordance with the present disclosure. The gas sensor 100 includes a housing 102 having a cavity 104 and vent hole 106 within the housing 102 and cavity 104. The housing 102 also may include a distributed element resonator 108 and an optional heating element 128, both of which are within the cavity 104. The distributed element resonator 108 has an input terminal 112 and output terminal 114 and is configured as a radio frequency (RF) distributed element resonator. The input terminal 112 is configured to receive a RF input signal 116 from a signal source 118 (that is in signal communication with the input terminal 112) and the output terminal 114 is configured to produce an output signal 120 that may be transmitted to a detector circuit 122 that is in signal communication with the output terminal 114.

In this example, the gas sensor 100 is configured to detect one or more gases 124 within an environment 126. This environment 126 may be within a vehicle, such as for example an aircraft. In the case of an aircraft, the environment 126 may be, for example, a cockpit, cabin, wings, etc. and the gas sensor 100 is configured to detect the gases 124. The gas sensor 100 is configured to detect the gases 124 that in many cases are non-detectable to humans on-board the aircraft. Examples of the types of gases 124 may include air, combustible hydrocarbons, carbon dioxide, volatile organic compounds, etc.

The gas sensor 100 may also include an optional heating element 128 that is located within the cavity 104. The optional heating element 128 may be in signal communication with an optional power supply 130. In this example, the optional heating element 128 includes a positive and a negative terminal to apply a DC voltage to the optional heating element 128 that may be a resistive heating element. The purpose of the optional heating element 128 is to heat the gas locally within the cavity 104 and at the distributed element resonator 108 such that two measurements can be made at approximately ambient temperature and an elevated temperature to improve selectivity of the measurements made by the detector circuit 122 in order to properly identify the gas type (of the gases 124) in the cavity 104 and as a result in the environment 126.

In these examples, the gas sensor 100 may be fabricated from two substrates utilizing a metal deposition process. The substrates may be dies on a wafer. In general, the gas sensor 100 including the optional heating element 128 may be constructed ambient or low temperature environments utilizing two substrates, each including, for example, silicon or glass and four (4) metallic layers each including, for example, gold, copper, silver, and titanium. For high temperature environments, the gas sensor 100 including the optional heating element 128 may be constructed utilizing two substrates, each including, for example, sapphire, diamond, or silicon carbide and four (4) metallic layers each including, for example, platinum, tungsten, and titanium.

In this example, the presently disclosed gas sensor 100 is unique because the gas sensor 100 has a resistive heating element (i.e., optional heating element 128) patterned under the cavity 104 that is machined in the first substrate with positive and negative terminals configured to apply the DC voltage 134 to the optional heating element 128 and the distributed element resonator 108 patterned on a top surface of the second substrate that permits frequencies within a given frequency band to pass from the input terminal 112 to the output terminal 114. The gas sensor 100 also includes a ground plane on a bottom surface of the second substrate to provide low loss signal propagation throughout the combined cavity 104 and distributed element resonator 108. The gas sensor 100 may also be constructed of high temperature compatible materials such as sapphire, diamond, or silicon carbide for the mechanical portions of the substrates and platinum, tungsten, or titanium for the electrical portions of the metallic layers. The gas sensor 100 may also be attached to electronics at an extended distance to allow the gas sensor 100 to operate in high temperature environments. As discussed earlier, the gas sensor 100 with the optional heating element 128 is configured to improve the gas selectivity by allowing for differential measurements of the gas in the cavity 104 at room temperature (i.e., ambient) and at an elevated temperature.

In an example of operation, the gas sensor 100 performs a method that includes initially receiving air, from the gases 124, through the vent hole 106 into the cavity 104. The distributed element resonator 108 is excited by the RF input signal 116 from the signal source 118 to radiate within the cavity 104 at a first resonant frequency. This produces the output signal 120, at the output terminal 114, at the first frequency that is transmitted to the detector circuit 122. As new gas (from the gases 124) appears in the environment 126, the new gas is received from the environment 126 into the cavity 104 through the vent hole 106, the resonant frequency of the excited distributed element resonator 108 changes to a second resonant frequency based on the change of permittivity from air to the new gas in the cavity 104. In this example, the distributed element resonator 108 produces the output signal 120 (at the output terminal 114) with the second resonate frequency that is passed to the detector circuit 122. The detector circuit 122 is configured to produce a gas type response signal 132 that indicates what type of gas that the new gas is. In this example, the signal source 118 may be a time variant signal generator (e.g., an alternating current (AC) voltage source) and the detector circuit 122 may be receiver.

The distributed element resonator 108 has a resonant length that is related to a permittivity of the gas received in the cavity 104. As the gas in the cavity 104 changes in concentration the effective permittivity of the gas in the cavity 104 changes. This change in permittivity causes the resonant frequency of the distributed element resonator 108 to change. In this example, there is a linear region where the output voltage of the output signal 120 is linearly proportional to the permittivity of the gas in the cavity 104. As a result, the sensitivity of the gas sensor 100 may be approximately equal to, for example, 128 millivolts per volt (mV/V).

Figure 2:
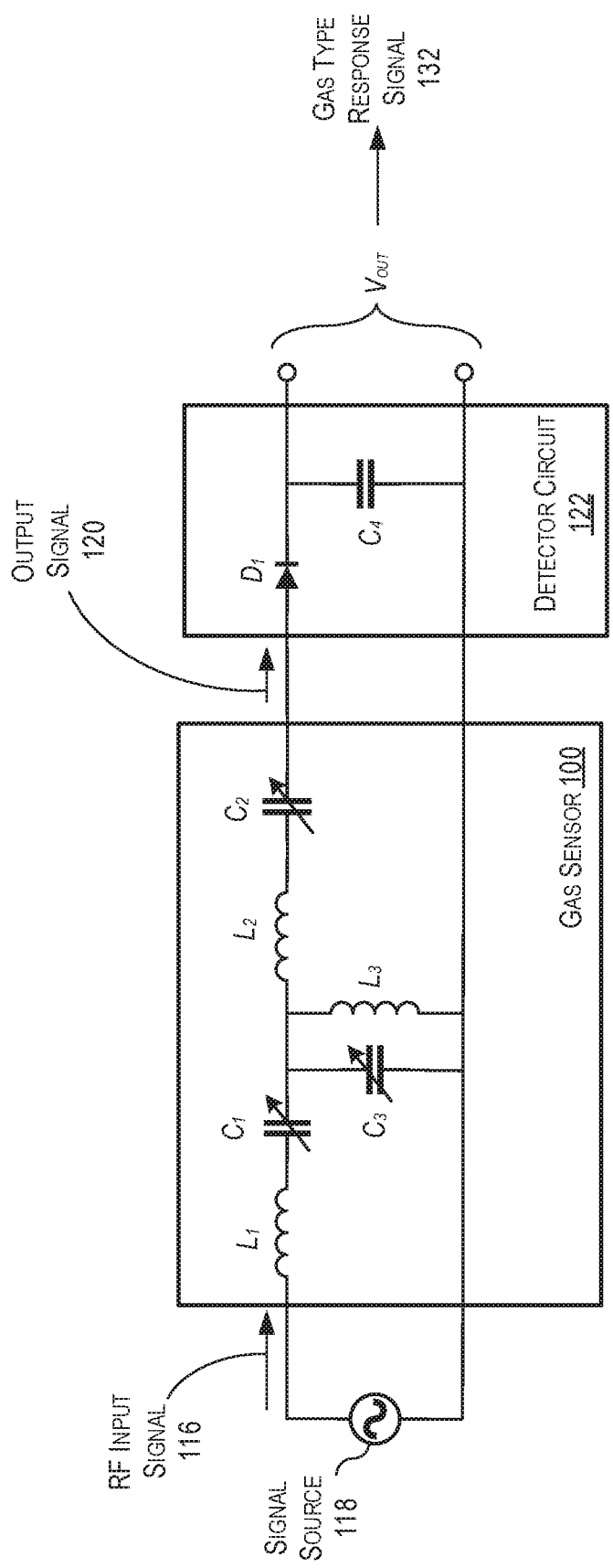
FIG. 2 is a schematic block diagram of an example of an implementation of the gas sensor shown in FIG. 1 in accordance with present disclosure.

Turning to FIG. 2, a schematic block diagram of an example of an implementation of the gas sensor 100 is shown in accordance with the present disclosure. In this example, the combined cavity 104 and distributed element resonator 108 are shown schematically as a lumped element model having series inductors $L_1$, $L_2$, series variable capacitors $C_1$ and $C_2$, and parallel inductor $L_3$ and variable capacitor $C_3$. In this example, the capacitive values of the variable capacitors $C_1$, $C_2$, and $C_3$ vary with the corresponding permittivity of the gas (as a result of concentration changes) in the cavity 104.

Also, in this example, the detector circuit 122 is shown as a receiver that may be implemented as an envelope detector circuit having a diode $D_1$ and parallel capacitor $C_4$. It is appreciated by those of ordinary skill in the art that as an envelope detector, the detector circuit 122 produces a direct current (DC) voltage signal ($V_{out}$) for the gas type response signal 132 that is the envelope voltage over frequency of the output signal 120. As a result, the produced $V_{out}$ of the gas type response signal 132 allows the identification of the type of gas present in the gas sensor 100 and correspondingly the environment 126.

It is appreciated by those of ordinary skill in the art that the circuits, components, modules, and/or devices of, or associated with, the gas sensor 100 are described as being in signal communication with each other, where signal communication refers to any type of communication and/or connection between the circuits, components, modules, and/or devices that allows a circuit, component, module, and/or device to pass and/or receive signals and/or information from another circuit, component, module, and/or device. The communication and/or connection may be along any signal path between the circuits, components, modules, and/or devices that allows signals and/or information to pass from one circuit, component, module, and/or device to another and includes wireless or wired signal paths. The signal paths may be physical, such as, for example, conductive wires, electromagnetic wave guides, cables, attached and/or electromagnetic or mechanically coupled terminals, semi-conductive or dielectric materials or devices, or other similar physical connections or couplings. Additionally, signal paths may be non-physical such as free-space (in the case of electromagnetic propagation) or information paths through digital components where communication information is passed from one circuit, component, module, and/or device to another in varying digital formats, without passing through a direct electromagnetic connection.

Figure 3:
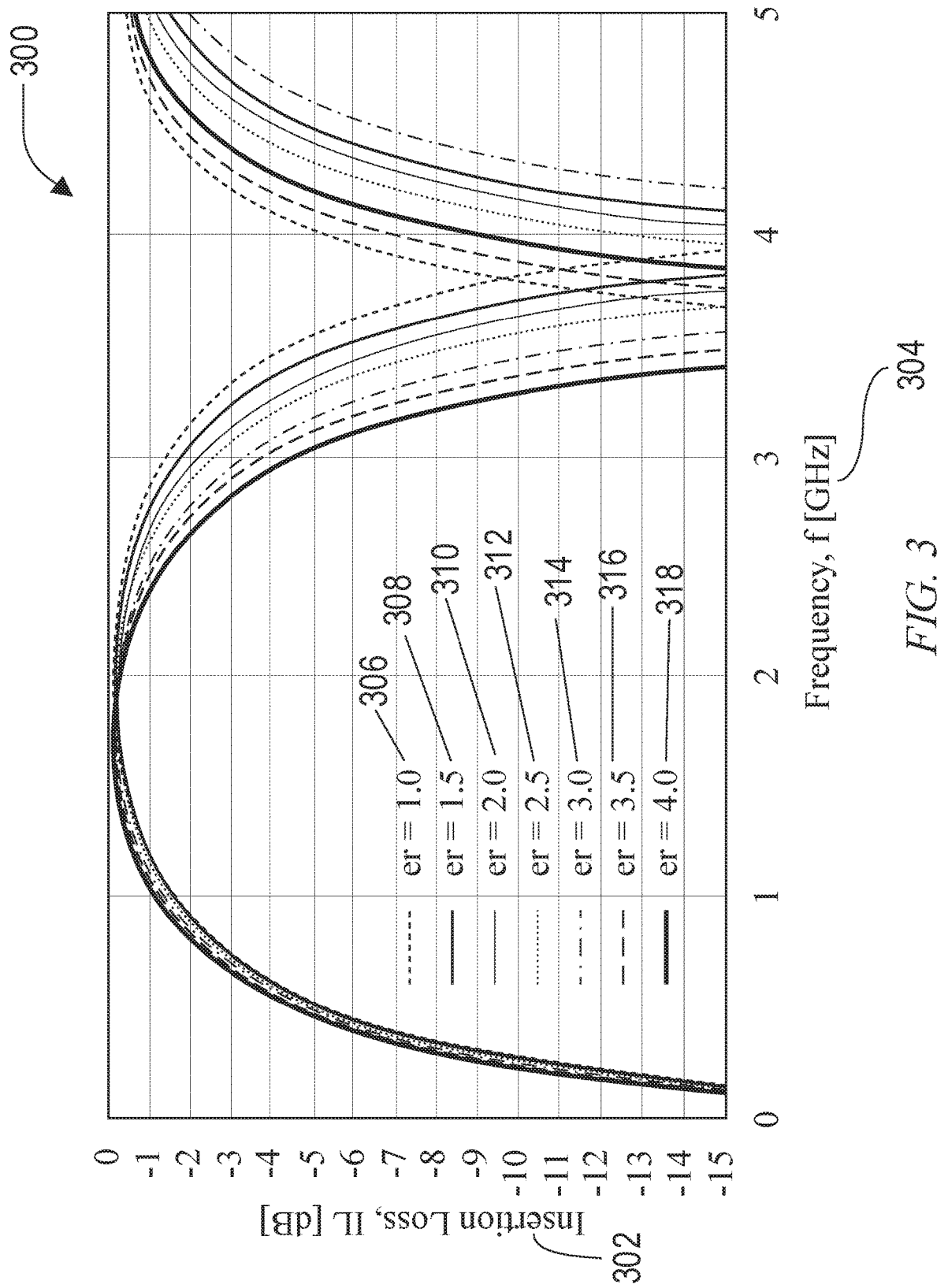
FIG. 3 is a graph of insertion loss in decibels (dB) versus operational frequency in gigahertz (GHz) for different plots of the permittivity of the type of gas in accordance with the present disclosure.

In FIG. 3, a graph 300 of insertion loss 302 in decibels (dB) versus operational frequency 304 in gigahertz (GHz) for different plots 306, 308, 310, 312, 314, 316, and 318 of the permittivity of the type of gas is shown in accordance with the present disclosure. The operational frequency 304 range of the graph 300 varies between 0 to 5 GHz and the insertion loss 302 range of the graph varies between −15 and 0 dB. In this example, the first plot 306 corresponds to a gas type that is air (with a relative permittivity $\varepsilon_r$ equal to 1.0), the second plot 308 corresponds to a gas type that has a relative permittivity equal to 1.5, the third plot 310 corresponds to gas type that has a relative permittivity equal to 2.0, the fourth plot 312 corresponds to a gas type that has a relative permittivity equal to 2.5, the fifth plot 314 corresponds to a gas type that has a relative permittivity equal to 3.0, the sixth plot 316 corresponds to a gas type that has a relative permittivity equal to 3.5, and the seventh plot 318 corresponds to a gas type that has a relative permittivity equal to 4.0.

Figure 4:
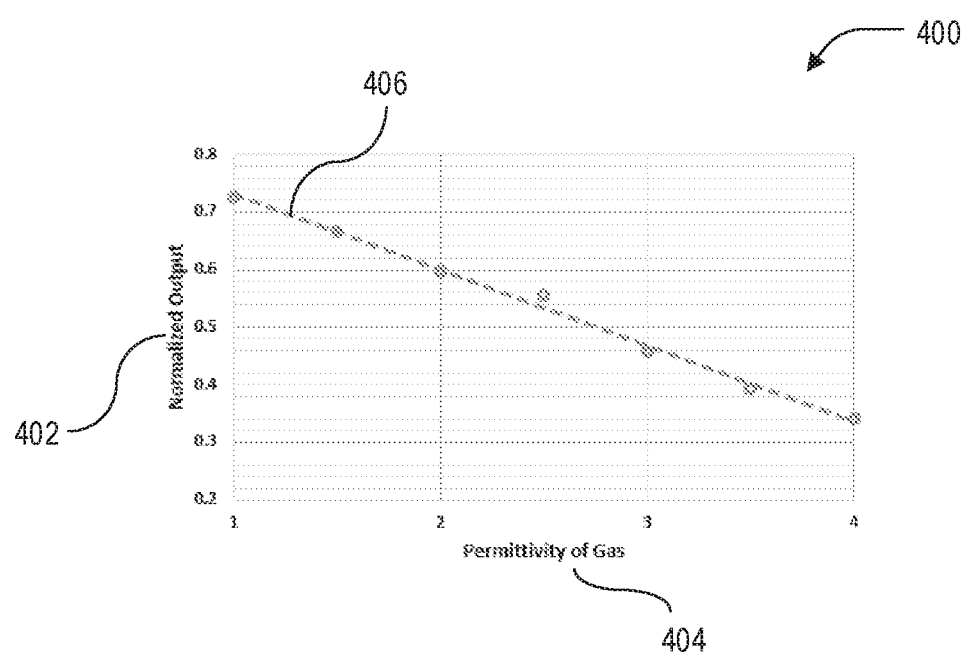
FIG. 4 is a graph of the normalized output shown in FIG. 2 versus the permittivity of the type of gas in accordance with the present disclosure.

In FIG. 4, a graph 400 of the normalized output 402 versus the permittivity 404 of the type of gas is shown in accordance with the present disclosure. In this example, a linear plot 406 is shown where normalized output 402 of $V_{out}$ is linearly proportional to the permittivity 404 of the gas type. As discussed previously, in this example, the sensitivity of the gas sensor 100 would be approximately 128 mV/V.

Figure 5A:
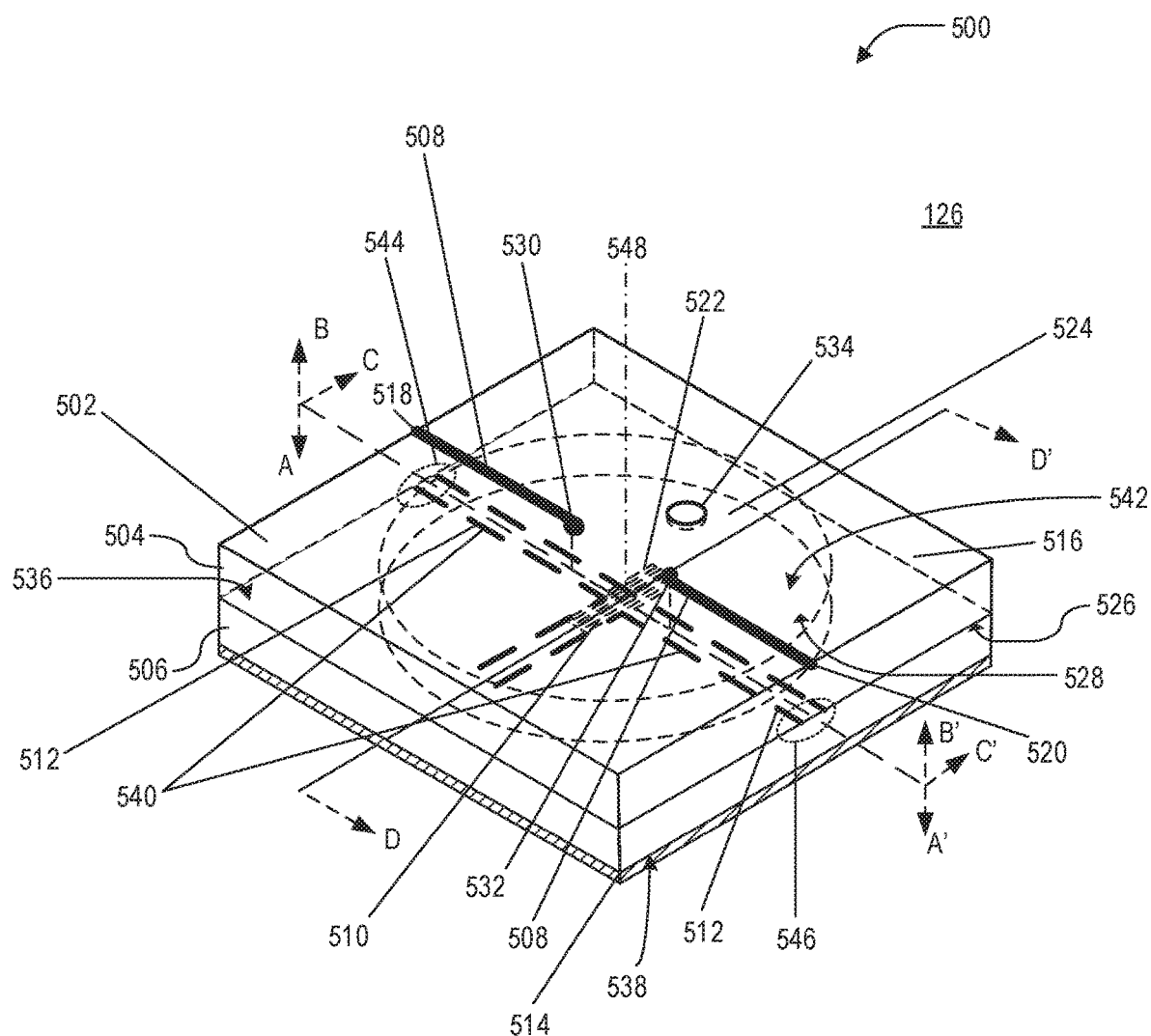
FIG. 5A is a perspective view of an example of an implementation of the gas sensor shown in FIGS. 1 and 2 in accordance with the present disclosure.

Turning to FIG. 5A, a perspective view of an example of an implementation of a gas sensor 500 is shown in accordance with the present disclosure. In this example, the gas sensor 500 includes a housing 502 comprising a first substrate 504, second substrate 506, a first metallic layer 508, second metallic layer 510, third metallic layer 512, and fourth metallic layer 514. The first metallic layer 508 is deposited on a top surface 516 of the first substrate 504 and is an electrical trace of a first terminal 518 and a second terminal 520 of the optional heating element 522. In this example, the first terminal 518 may be a positive DC voltage terminal and the second terminal 520 may be a negative DC voltage terminal, or vice versa.

The first substrate 504 includes the cavity 524 that is shown with hidden lines. The cavity 524 may be etched out of a bottom surface 526 of the first substrate 504 forming a top surface 528 of the cavity 524. The optional heating element 522 may be formed by depositing the second metallic layer 510 on the top surface 528 of the cavity 524. The optional heating element 522 is in signal communication with the first terminal 518 and a second terminal 520 through a first via 530 and second via 532 that are holes through the top surface 516 of the first substrate 504 and top surface 528 of the cavity 524, which are filled with the metal from the first metallic layer 508. The first substrate 504 also includes a vent hole 534 that is also an opening from through the top surface 516 of the first substrate 504 and top surface 528 of the cavity 524 and is configured to allow gas to enter the cavity 524 from the environment 126.

The second substrate 506 has a top surface 536 and a bottom surface 538. The distributed element resonator 540 may be formed by depositing the third metallic layer 512 on the top surface 536 of the second substrate 506 that corresponds to a bottom surface 542 of the cavity 524. The fourth metallic layer 514 may be deposited on the bottom surface 538 of the second substrate 506 to form a ground plane.

In this example, the cavity 524 is shown as being a circular cavity but it is appreciated by those of ordinary skill in the art that the cavity 524 may alternatively be a rectangular, triangular, or elliptical cavity based on the design preferences of the gas sensor 500. Moreover, the distributed element resonator 540 may be, for example, a stub filter that includes a shorted quarter-wave stub or an open quarter-wave stub, a microstrip patch resonator element, or a coupled line filter that includes an interdigitated filter, hairpin filter, capacitive gap filter, etc. The distributed element resonator 540 includes the input terminal 544 and the output terminal 546 that are part of the third metallic layer 512. In this example, the gas sensor 500 is shown to have a central axis 548.

Figure 5B:
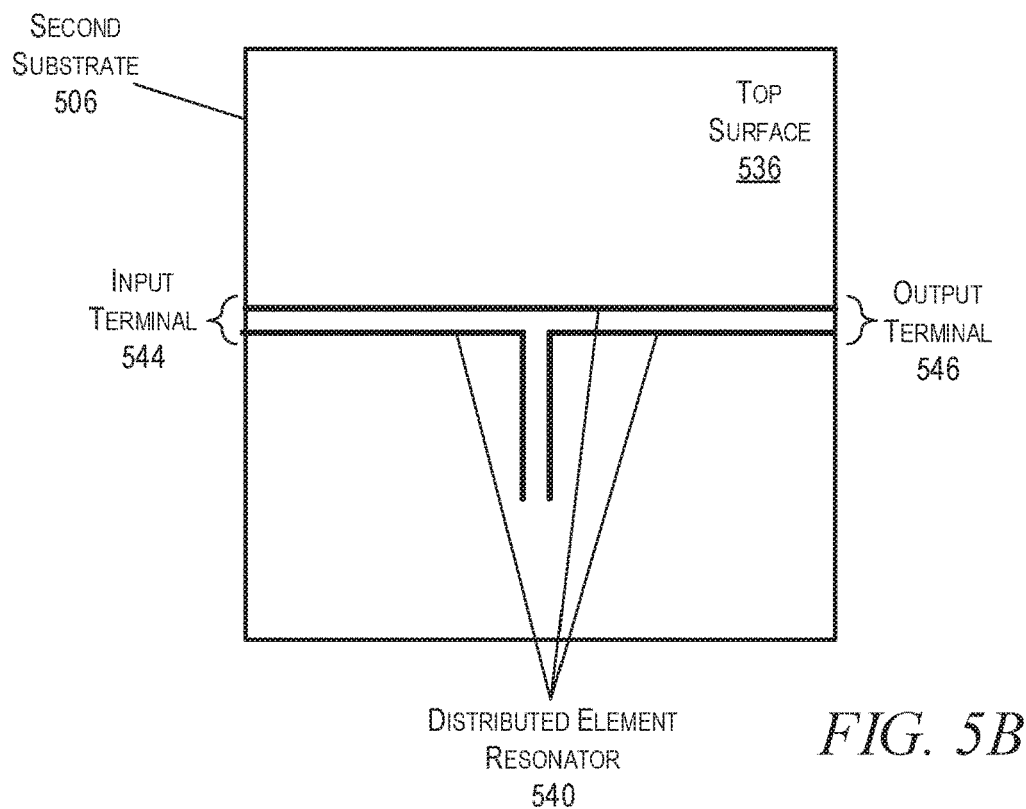
FIG. 5B is a cross-section top view of the gas sensor shown in FIG. 5A in accordance with the present disclosure.

Turning to FIG. 5B, a cross-section top view along a cutting plane AA' of the gas sensor 500 is shown in accordance with the present disclosure. In this view, the distributed element resonator 540 is shown patterned on the top surface 536 of the second substrate 506.

Figure 5C:
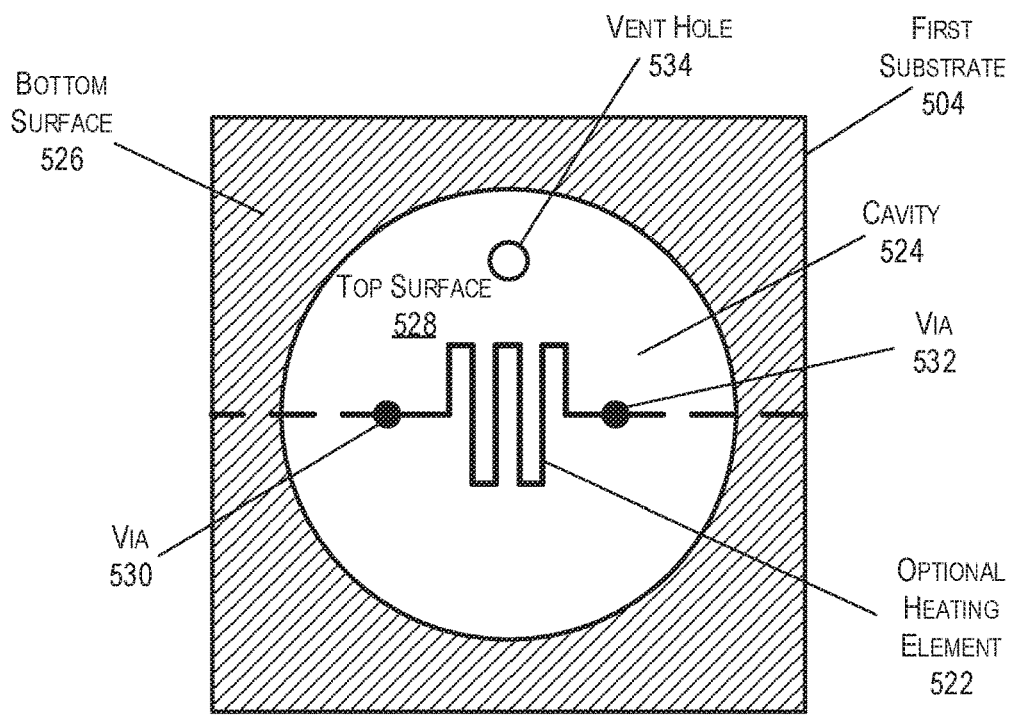
FIG. 5C is a cross-section bottom view of the gas sensor shown in FIGS. 5A and 5B in accordance with the present disclosure.

In FIG. 5C, a cross-section bottom view along the cutting plane BB' of the gas sensor 500 is shown in accordance with the present disclosure. In this view, the optional heating element 522 is shown patterned on the top surface 528 of the cavity 524, where the cavity is etched into the bottom surface 526 of the first substrate 504. The top surface 528 of the cavity 524 is also shown to have the vent hole 534, first via 530, and second via 532.

Figures 5D, 5E:
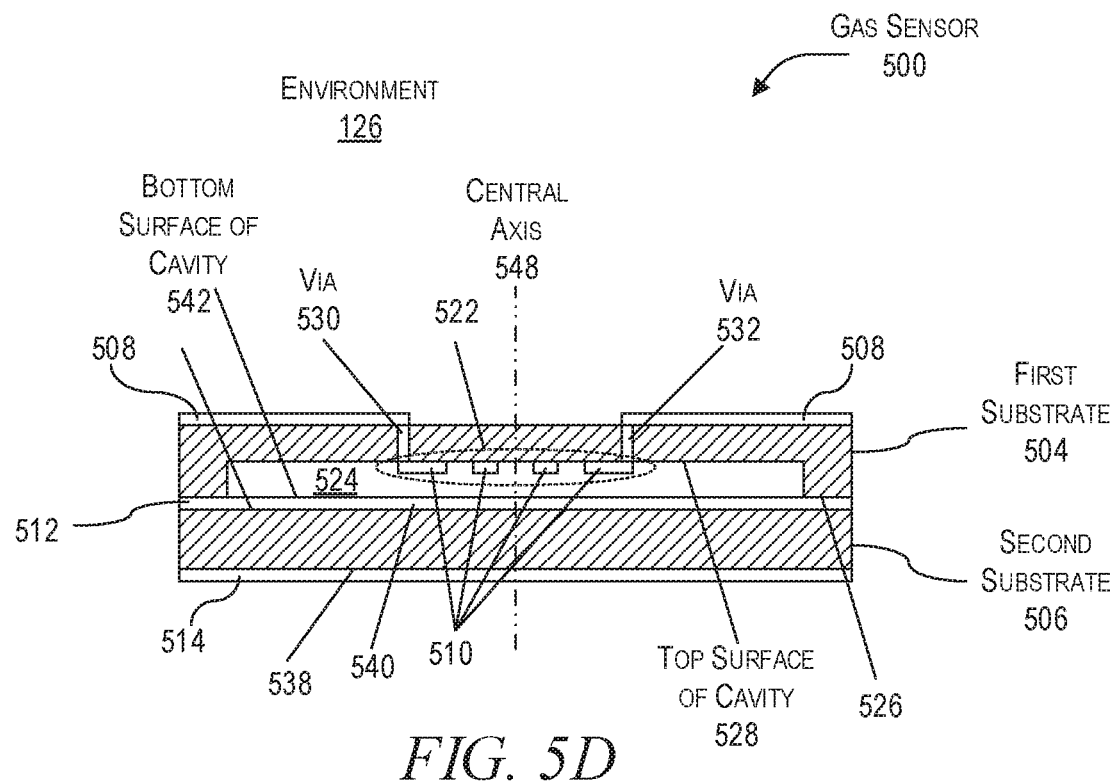
FIG. 5D is a cross-section front view of the gas sensor shown in FIGS. 5A through 5C in accordance with the present disclosure.
FIG. 5E is a cross-section side view of the gas sensor shown in FIGS. 5A through 5D in accordance with the present disclosure.

In FIG. 5D, a cross-section front view along cutting plane CC' of the gas sensor 500 is shown in accordance with the present disclosure. In this view, the optional heating element 522 is shown patterned on the top surface 528 of the cavity 524 and the distributed element resonator 540 is shown patterned on the top surface 536 of the second substrate 506, which corresponds to the bottom surface 542 of the cavity 524. The fourth metallic layer 514 is again shown as the ground plane deposited on the bottom surface 538 of the second substrate 506. The first via 530 and second via 532 are shown electrically connecting the first metallic layer 508 to the second metallic layer 510.

FIG. 5E is a cross-section side view along cutting plane DD' of the gas sensor 500 shown in in accordance with the present disclosure. In this view, the optional heating element 522 is shown patterned on the top surface 528 of the cavity 524 and the distributed element resonator 540 is shown patterned on the top surface 536 of the second substrate 506, which corresponds to the bottom surface 542 of the cavity 524. The fourth metallic layer 514 is shown as a ground plane deposited on the bottom surface 538 of the second substrate 506. The vent hole 534 is shown as an opening from the environment 126 to the cavity 524.

Figure 6:
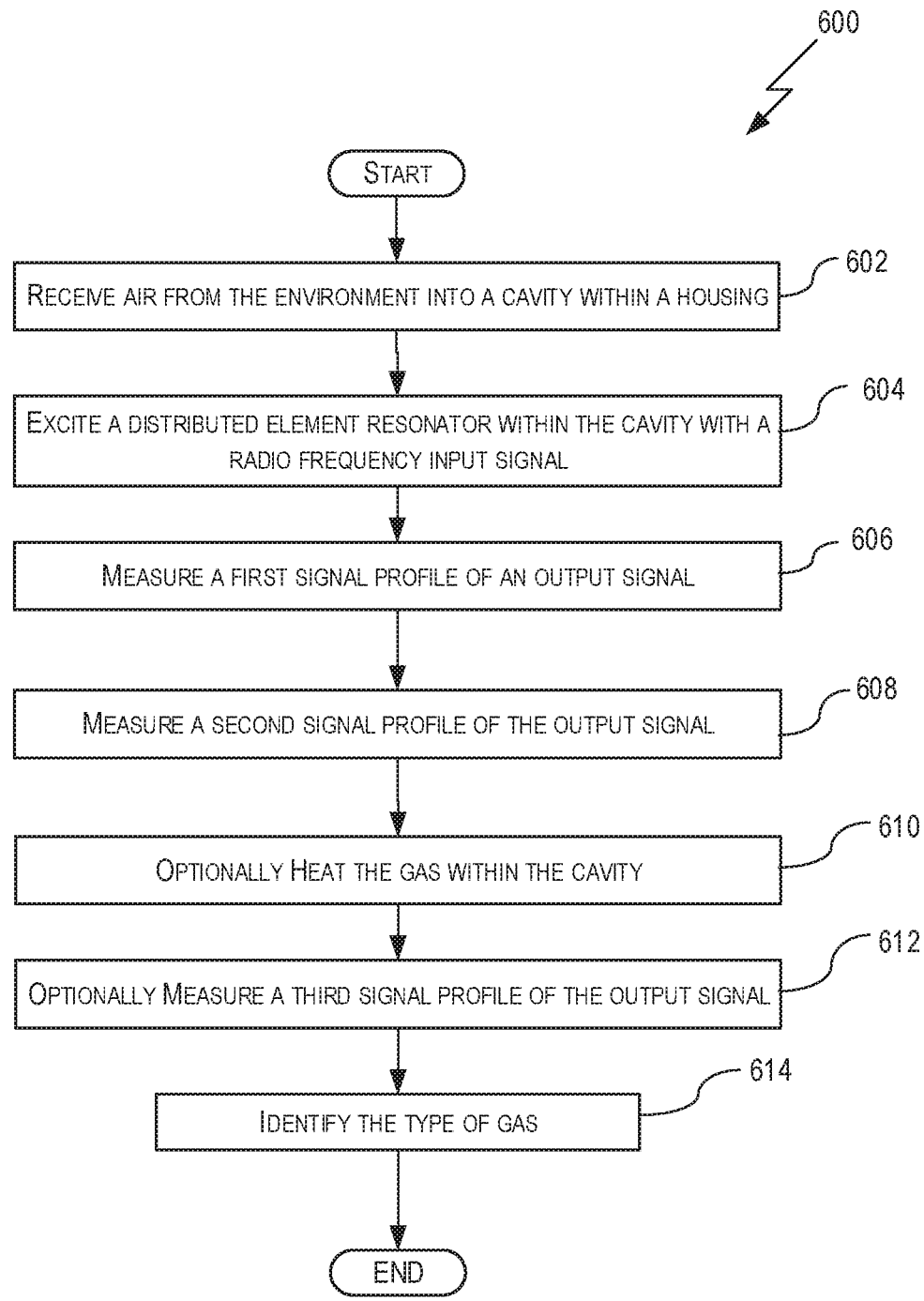
FIG. 6 is a flowchart of an example implementation of a method of operation of the gas sensor shown in FIGS. 1-5D in accordance with the present disclosure.

Turning to FIG. 6, a flowchart of an example implementation of a method 600 of operation of the gas sensor 100, 500 is shown in accordance with the present disclosure. The method 600 starts by receiving 602 air from the environment 126 into the cavity within the housing. The distributed element resonator is excited 604 with an RF input signal. An output signal is produced, and a first signal profile of the output signal is measured 606. A gas is then received from the environment 126 while the distributed element resonator is still excited in the cavity. A second signal profile is measured 608 from the output signal produced by the gas sensor. The gas in the cavity is then optionally heated 610 with the optional heating element and a third signal profile is optionally measured 612 from the output signal. The type of gas in the cavity is then identified 614 and the process ends.

Figure 7:
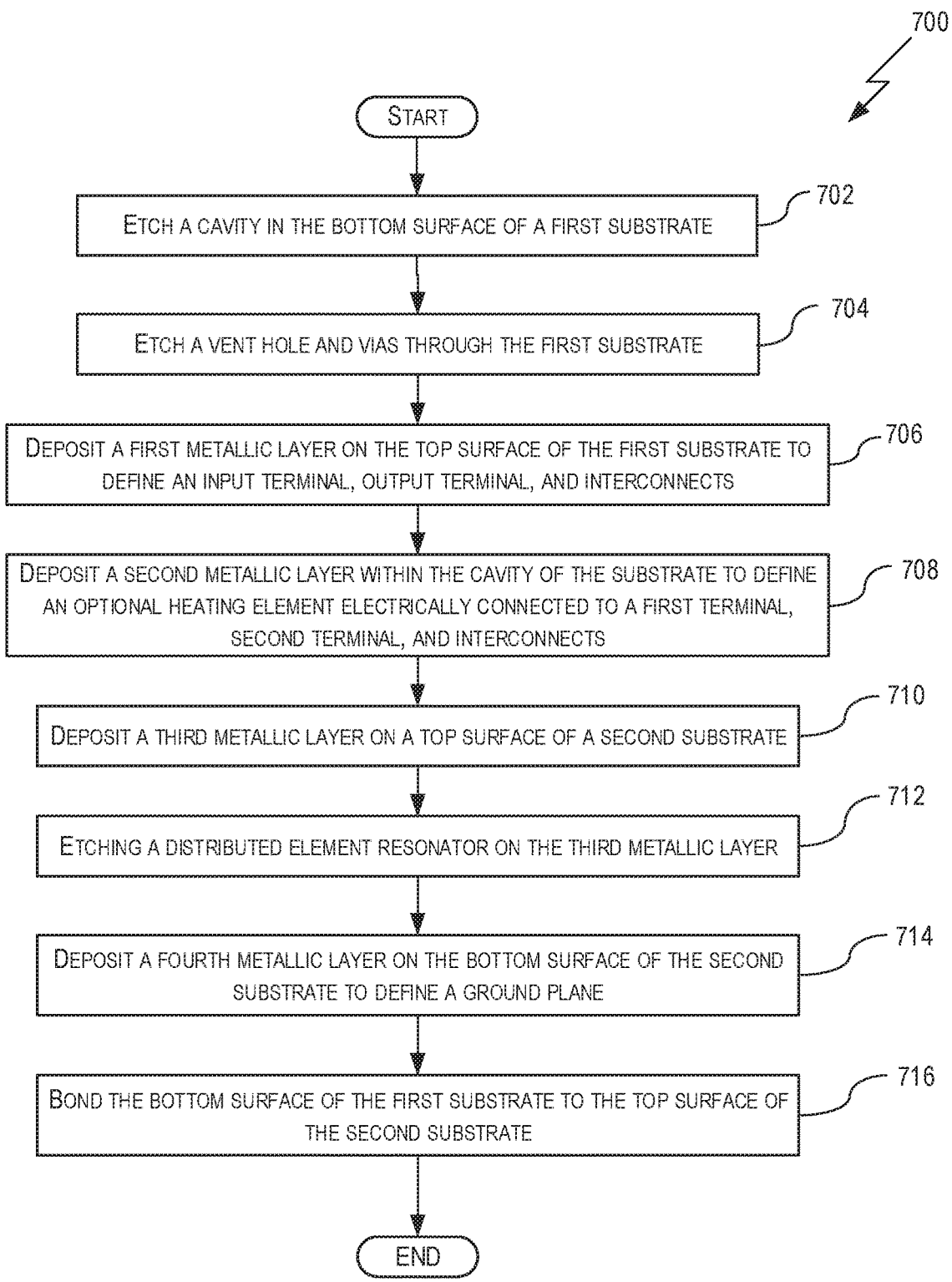
FIG. 7 is a flowchart of an example implementation of a method of fabricating the gas sensor shown in FIGS. 1-5D in accordance with the present disclosure.

In FIG. 7, a flowchart of an example implementation of a method 700 for fabricating the gas sensor 100, 500 is in accordance with the present disclosure. The method 700 starts by etching 702 a cavity 524 in the bottom surface 526 of the first substrate 504. The vent hole 534, first via 530, and second via 532 are then etched 704 through the first substrate 504. The first metallic layer 508 is then deposited 706 on the top surface 516 of the first substrate 504. The second metallic layer 510 is deposited 708 within the cavity 524 of the first substrate 504 to define the optional heating element 522 that is electrically connected to the first via 530 and second via 532, and the first terminal 518 and second terminal 520 of the optional heating element 522. The third metallic layer 512 is then deposited 710 on the top surface 536 of the second substrate 506. The distributed element resonator 540 is then etched 712 on the third metallic layer 512. The fourth metallic layer 514 is then deposited 714 on the bottom surface 538 of the second substrate 506 to define a ground plane. Then the bottom surface 526 of the first substrate 504 is bonded 716 to the top surface 536 of the second substrate 506 and the method ends.

Based on the method 700 described in relation to FIG. 7, FIGS. 8A-9G show the deposition stack up and bonding process along the central axis 548 in fabricating the gas sensor 500 in accordance with the present disclosure. In this example, the disposition method may include either a thin film deposition process or a printing process. In the case of thin film deposition process, the process may include chemical deposition methods that include, for example, chemical vapor deposition (CVD), plasma enhanced CVD (PECVD), atomic layer deposition (ALD), or molecular layer deposition (MLD). The thin film deposition process may also include, for example, physical deposition methods that include physical vapor deposition (PVD), thermal evaporation, and sputtering deposition. In the case of printing process, the printing methods may include, for example, Gravure printing, screen printing, ink-jet printing, liquid dispense, and microcontact printing.

Figure 8A:
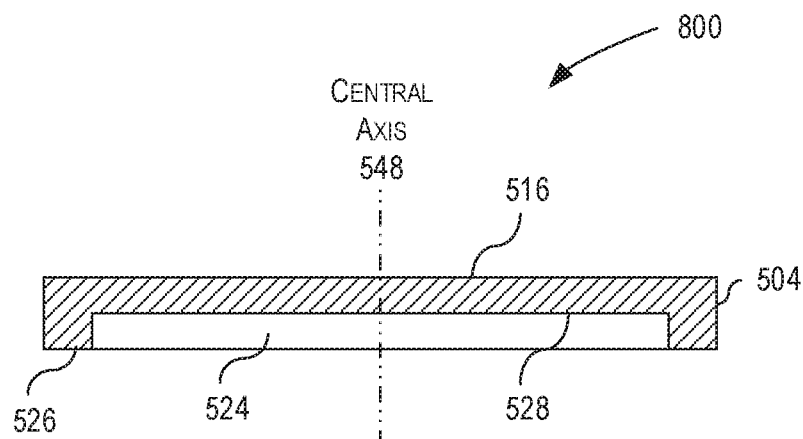
FIG. 8A is a cross-sectional front view of a first section of the gas sensor in accordance with the present disclosure.
Figure 8B:
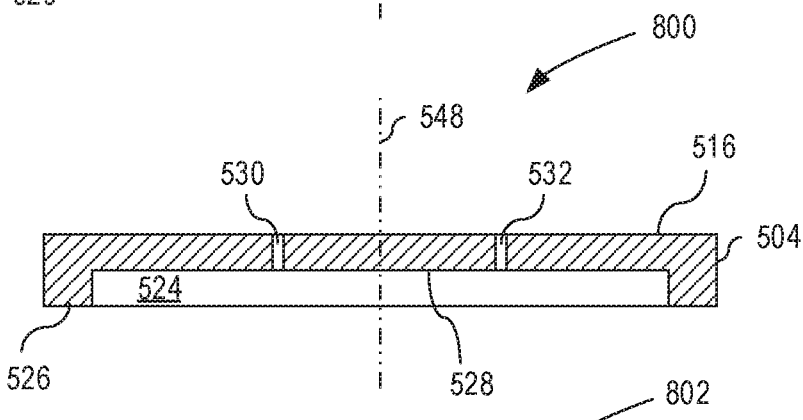
FIG. 8B is a cross-sectional front view of the first section with etched vias in accordance with the present disclosure.
Figure 8C:
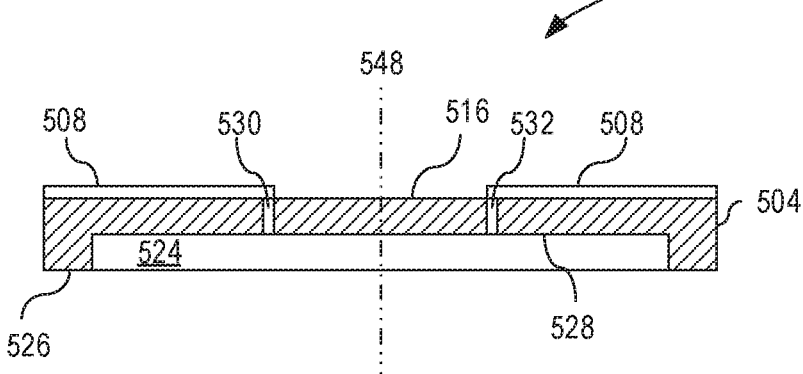
FIG. 8C is a cross-sectional front view of a first combination of the first section and a deposited first metallic layer in accordance with the present disclosure.
Figure 8D:
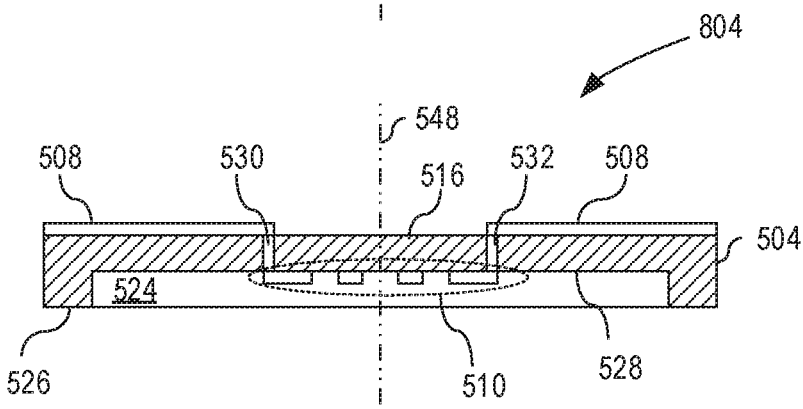
FIG. 8D is a cross-sectional front view of a second combination with the first combination and a deposited second metallic layer in accordance with the present disclosure.

Turning to FIG. 8A, a cross-sectional front view of a first section 800 of the gas sensor 500 is shown in accordance with the present disclosure. The cavity 524 is etched into the bottom surface 526 of the first substrate 504. In FIG. 8B, the first section 800 is further etched to form the first via 530 and second via 532 in the first substrate 504. In FIG. 8C, a first combination 802 of the first section 800 and the deposited first metallic layer 508 is shown in accordance with the present disclosure. The first metallic layer 508 is deposited on the top surface 516 of the first substrate 504 and into the first via 530 and second via 532 to form the first combination 802. The first metallic layer 508 form the first terminal 518 and second terminal 520. In FIG. 8D, a second combination 804 is shown of the first combination 802 and the deposited second metallic layer 510 in accordance with the present disclosure. The second combination 804 is formed when the second metallic layer 510 is deposited on the top surface 528 of the cavity 524 and is electrically connected to the first via 530 and second via 532.

Figure 8E:
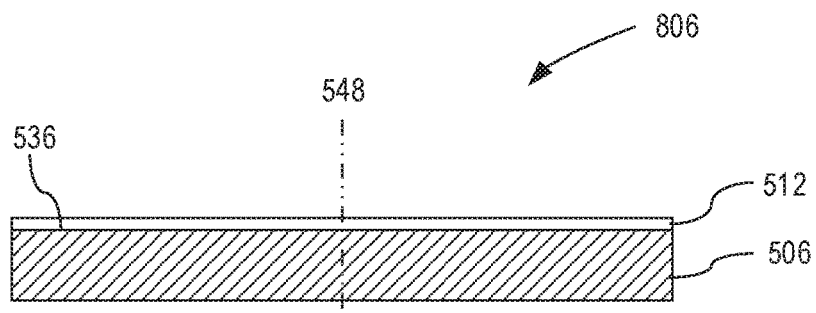
FIG. 8E is a cross-sectional front view of a third combination having the second substrate and a deposited third metallic layer in accordance with the present disclosure.
Figure 8F:
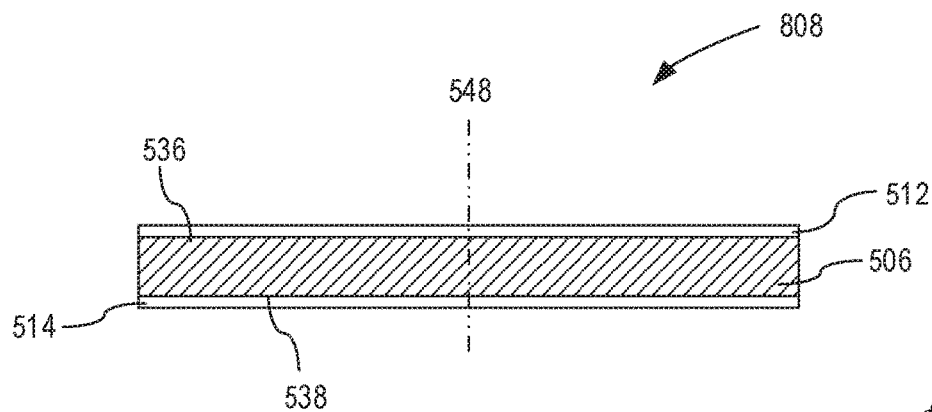
FIG. 8F is a cross-sectional front view of a fourth combination and a deposited fourth metallic layer in accordance with the present disclosure.
Figure 8G:
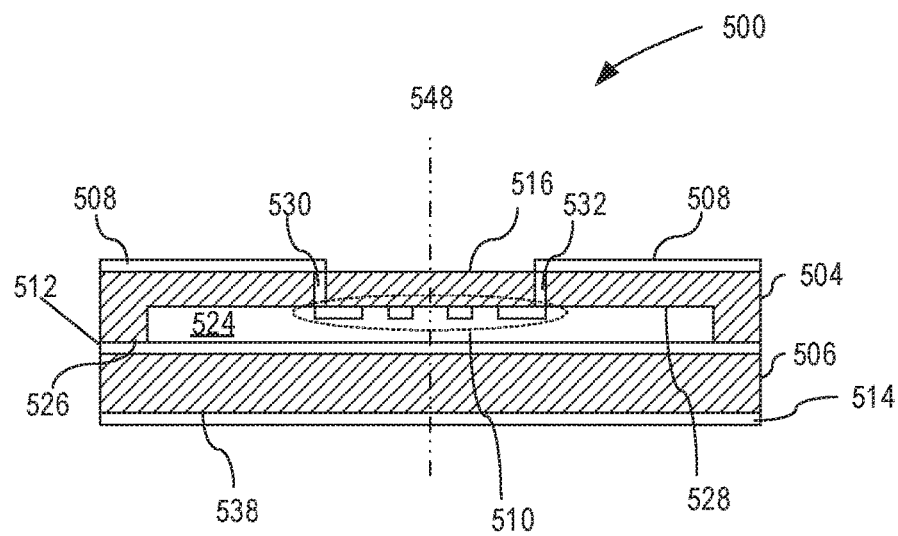
FIG. 8G is a cross-sectional front view of a fifth combination of the bonded second combination and the fourth combination in accordance with the present disclosure.

In FIG. 8E, a cross-sectional front view of a third combination 806 of the second substrate 506 and the deposited third metallic layer 512 is shown in accordance with the present disclosure. In this example, the third metallic layer 512 is deposited on the top surface 536 of the second substrate 506 forming the third combination 806. The third metallic layer 512 is then etched to produce the distributed element resonator 540. In FIG. 8F, a fourth combination 808 of the third combination 806 and the deposited fourth metallic layer 514 is shown in accordance with the present disclosure. In this example, the fourth metallic layer 514 is deposited on the bottom surface 538 of the second substrate 506. The fourth metallic layer 514 is configured as a ground plane. In FIG. 8G, a fifth combination of the bonded second combination 804 and the fourth combination 808 is shown in accordance with the present disclosure. In this example, the fifth combination is the gas sensor 500.

Figure 9A:
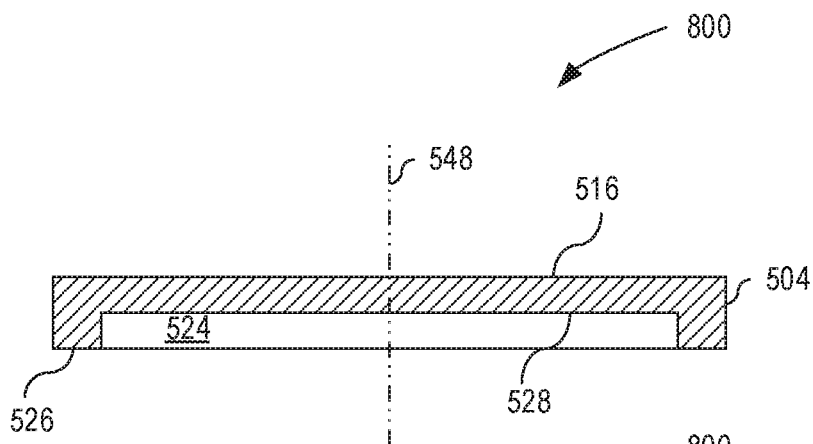
FIG. 9A is a cross-sectional side view of the first section of the gas sensor shown in FIG. 8A in accordance with the present disclosure.
Figure 9B:
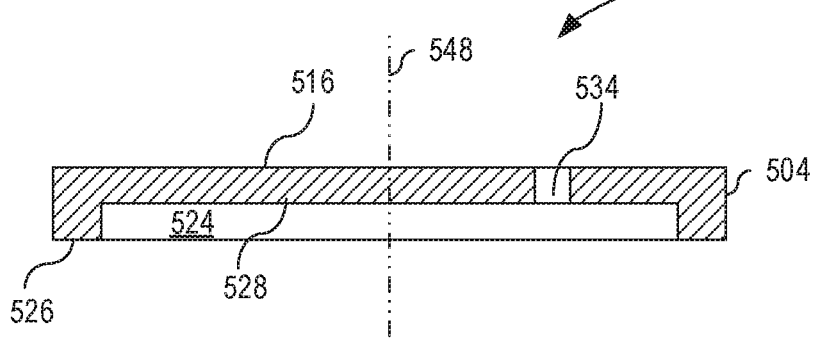
FIG. 9B is a cross-sectional side view of the first section of the gas sensor with an etched vent hole shown in FIG. 8B in accordance with the present disclosure.
Figure 9C:
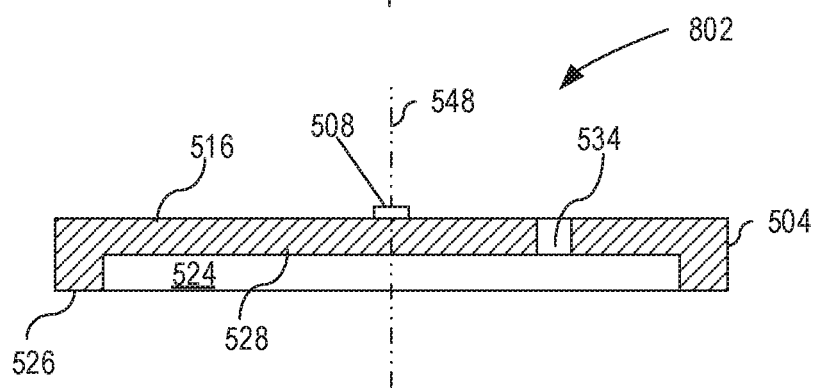
FIG. 9C is a cross-sectional side view of a first combination of the first section and the deposited first metallic layer shown in FIG. 8C in accordance with the present disclosure.
Figure 9D:
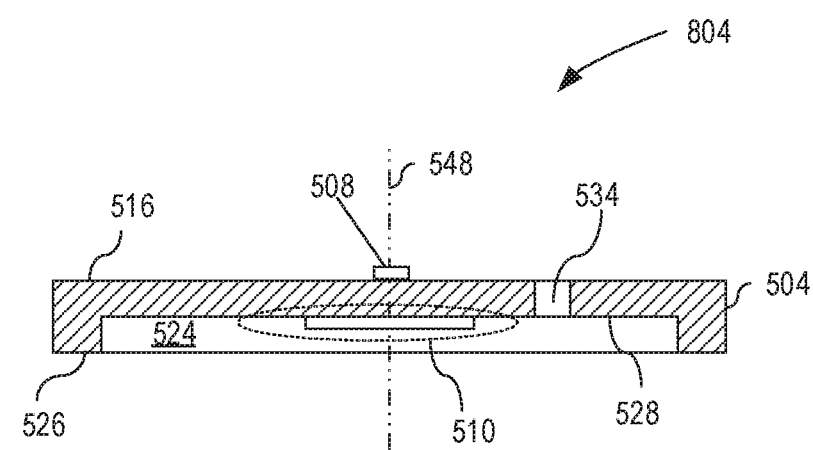
FIG. 9D is a cross-sectional side view of the second combination of the first combination and the deposited second metallic layer shown in FIG. 8D in accordance with the present disclosure.

Turning FIG. 9A, a cross-sectional side view of the first section 800 of the gas sensor 500 is shown in accordance with the present disclosure. Similar to the first section 800 shown in FIG. 8A, the cavity 524 is etched into the bottom surface 526 of the first substrate 504. In FIG. 9B, the first section 800 is shown with the etched vent hole 534 shown in accordance with the present disclosure. In this example, the vent hole 534 may be etched with the first via 530 and second via 532 shown in FIG. 8B. Similar to FIG. 8C, in FIG. 9C, the first combination 802 of the first section 800 and the deposited first metallic layer 508 is shown in accordance with the present disclosure. In FIG. 9D, the second combination 804 of the first combination 802 and the deposited second metallic layer 510 is shown in accordance with the present disclosure. Again, the second metallic layer 510 is deposited on the top surface 528 of the cavity 524 and is electrically connected to the first metallic layer 508 through the first via 530 and second via 532.

Figure 9E:
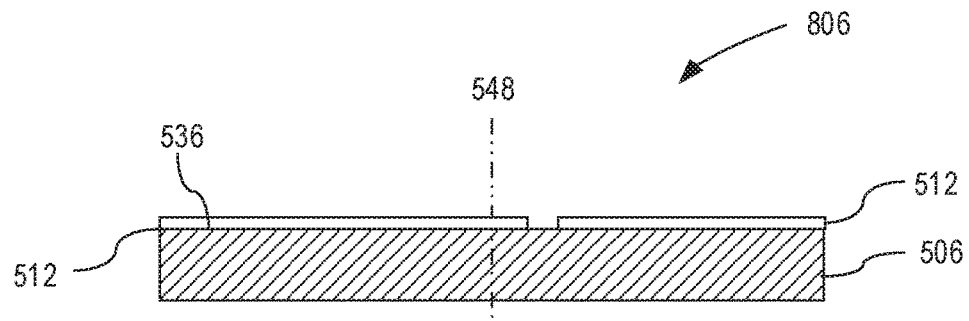
FIG. 9E is a cross-sectional side view of the third combination of the second substrate and the deposited third metallic layer shown in FIG. 8E in accordance with the present disclosure.
Figure 9F:
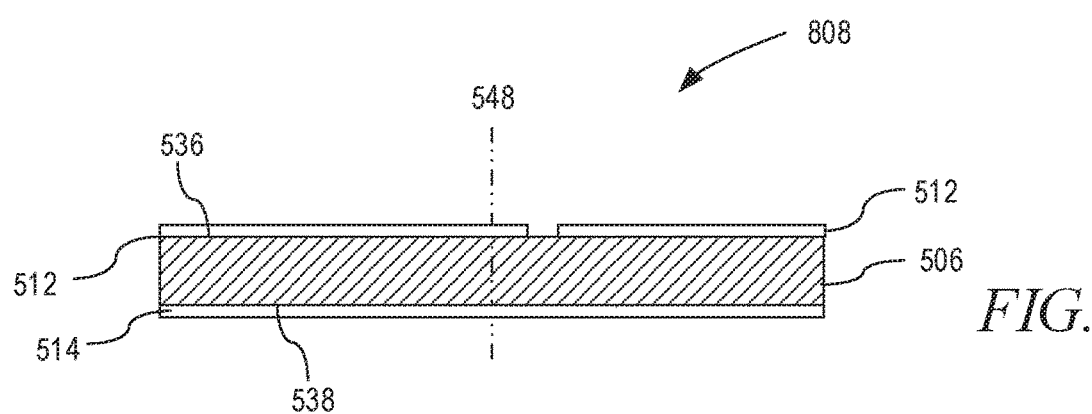
FIG. 9F is a cross-sectional side view of the fourth combination of the second combination and the deposited fourth metallic layer shown in FIG. 8F in accordance with the present disclosure.
Figure 9G:
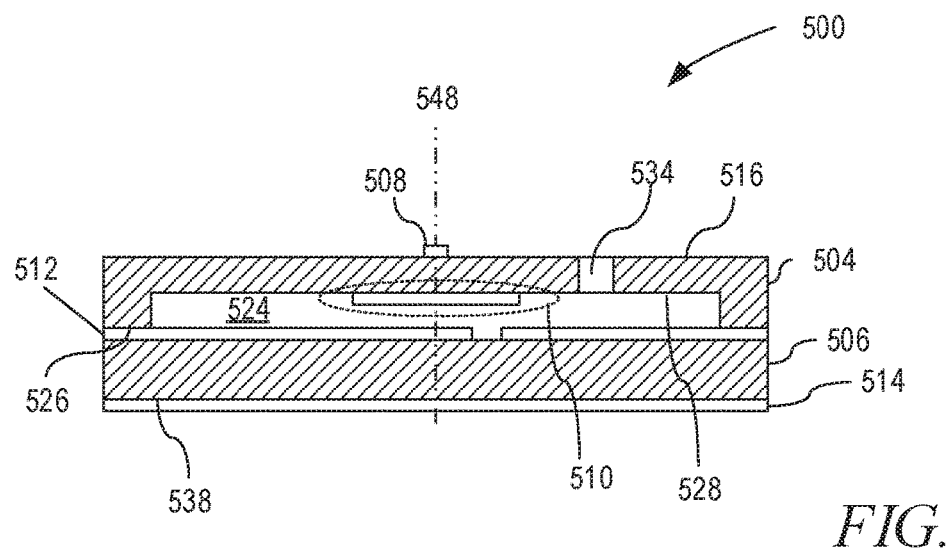
FIG. 9G is a cross-sectional side view of the fifth combination of the bonded second combination and the fourth combination in accordance with the present disclosure.

Similar to FIG. 8E, in FIG. 9E, a cross-sectional side view of the third combination 806 of the second substrate 506 and the deposited third metallic layer 512 is shown in accordance with the present disclosure. Again, the third metallic layer 512 is deposited on the top surface 536 of the second substrate 506 and then etched to produce the distributed element resonator 540. In FIG. 9F, the fourth combination 808 of the third combination 806 and the deposited fourth metallic layer 514 is shown in accordance with the present disclosure. In this example, the fourth metallic layer 514 is deposited on the bottom surface 538 of the second substrate 506 and is configured as a ground plane. In FIG. 9G, the fifth combination of the bonded second combination 804 and the fourth combination is shown in accordance with the present disclosure, where the fifth combination is the gas sensor 500.

It will be understood that various aspects or details of the disclosure may be changed without departing from the scope of the disclosure. It is not exhaustive and does not limit the claimed disclosures to the precise form disclosed. Furthermore, the foregoing description is for the purpose of illustration only, and not for the purpose of limitation. Modifications and variations are possible in light of the above description or may be acquired from practicing the disclosure. The claims and their equivalents define the scope of the disclosure. Moreover, although the techniques have been described in language specific to structural features and/or methodological acts, it is to be understood that the appended claims are not necessarily limited to the features or acts described. Rather, the features and acts are described as example implementations of such techniques.

Further, the disclosure comprises embodiments according to the following clauses.

Clause 1. A gas sensor for detecting a gas in an environment, the gas sensor comprising: a housing having a cavity and a vent hole within the housing, wherein the cavity includes a bottom surface, and a top surface, wherein the housing is configured to receive the gas from the environment into the cavity through the vent hole; and a distributed element resonator within the cavity, wherein the distributed element resonator has an input terminal configured to receive an radio frequency input signal and an output terminal configured to produce an output signal.

Clause 2. The gas sensor of clause 1, wherein the distributed element resonator is a radio frequency distributed element resonator on a bottom surface of a substrate, where the bottom surface of the substrate corresponds to the bottom surface of the cavity.

Clause 3. The gas sensor of clause 2, wherein the distributed element resonator is a stub filter that includes a coupled line filter that includes an interdigitated filter, hairpin filter, or capacitive gap filter.

Clause 4. The gas sensor of clause 2, wherein the distributed element resonator is a quarter-wave stub distributed element that includes a shorted quarter-wave stub element resonator or an open quarter-wave stub element resonator.

Clause 5. The gas sensor of clause 2, wherein the distributed element resonator is a microstrip patch resonator element.

Clause 6. The gas sensor of clause 1, further comprising a heating element within the cavity, wherein the heating element is configured to heat the gas within the cavity.

Clause 7. The gas sensor of clause 6, wherein the heating element is a resistive heating element patterned on the top surface of the cavity.

Clause 8. The gas sensor of clause 1, wherein the cavity and the distributed element resonator are configured as a cavity resonator and the cavity is configured as a circular cavity, rectangular cavity, triangular cavity, or elliptical cavity.

Clause 9. The gas sensor of clause 1, wherein the housing includes a substrate fabricated with silicon or glass and wherein the distributed element resonator is fabricated with gold, copper, silver, or titanium.

Clause 10. The gas sensor of clause 1, wherein the gas sensor is configured to operate in a high temperature environment, wherein the housing includes a substrate fabricated with sapphire, diamond, or silicon carbide, and wherein the distributed element resonator is fabricated with platinum, tungsten, or titanium.

Clause 11. The gas sensor of clause 1, further including an detector circuit (that may be, for example, an envelope detector) in signal communication with the output terminal, wherein the input terminal is configured to receive the radio frequency input signal.

Clause 12. A method for detecting a gas in an environment with a gas sensor, the method comprising: receiving the gas from the environment into a cavity within a housing; exciting a distributed element resonator within the cavity with a radio frequency input signal; and measuring an output signal from an output terminal in signal communication with the distributed element resonator.

Clause 13. The method of clause 12, further comprising: receiving air in the cavity prior to receiving the gas in the cavity, wherein measuring the output signal includes measuring a first signal profile corresponding to the air in the cavity; and measuring a second signal profile corresponding to the gas in the cavity.

Clause 14. The method of clause 13, further comprising identifying a type of gas from measuring the output signal.

Clause 15. The method of clause 14, wherein measuring the output signal includes envelope detecting the output signal with an envelope detector.

Clause 16. The method of clause 13, further comprising: heating the gas within the cavity; measuring a third signal profile corresponding to the heated gas in the cavity; and identifying a type of gas from measuring the second signal profile and the third signal profile.

Clause 17. A method for fabricating a gas sensor utilizing a deposition process, the method comprising: etching a cavity in a first substrate having a top surface and a bottom surface, wherein the cavity is etched on the bottom surface of the first substrate, and wherein the cavity has a top surface; etching a vent hole through the top surface of the first substrate and top surface of the cavity; depositing a first metallic layer on a second substrate, wherein the second substrate has a top surface and a bottom surface, and the first metallic layer is deposited on the top surface of the second substrate; etching a distributed element resonator on the first metallic layer; depositing a second metallic layer on the bottom surface of the second substrate to define a ground plane; and bonding the bottom surface of the first substrate to the top surface of the second substrate.

Clause 18. A method of clause 17, further comprising: etching a first via and second via through the top surface of the first substrate and the top surface of the cavity; depositing a third metallic layer on the top surface of the first substrate and first via and the second via to define an input terminal, output terminal, and interconnects; and depositing a fourth metallic layer within the etched cavity at the top surface of the cavity to define a heating element that is electrically connected to the interconnects.

Clause 19. The method of clause 18, wherein the first substrate and second substrate are fabricated with silicon or glass and wherein the first metallic layer, second metallic layer, third metallic layer, and fourth metallic layer is gold, copper, silver, or titanium.

Clause 20. The method of clause 18, wherein the gas sensor is configured to operate in a high temperature environment, wherein the first substrate and second substrate are fabricated with sapphire, diamond, or silicon carbide, and wherein the first metallic layer, second metallic layer, third metallic layer, and fourth metallic layer is platinum, tungsten, or titanium.

To the extent that terms "includes," "including," "has," "contains," and variants thereof are used herein, such terms are intended to be inclusive in a manner similar to the term "comprises" as an open transition word without precluding any additional or other elements. Moreover, conditional language such as, among others, "can," "could," "might" or "may," unless specifically stated otherwise, are understood within the context to present that certain examples include, while other examples do not include, certain features, elements and/or steps. Thus, such conditional language is not generally intended to imply that certain features, elements and/or steps are in any way required for one or more examples or that one or more examples necessarily include logic for deciding, with or without user input or prompting, whether certain features, elements and/or steps are included or are to be performed in any particular example. Conjunctive language such as the phrase "at least one of X, Y or Z," unless specifically stated otherwise, is to be understood to present that an item, term, etc. may be either X, Y, or Z, or a combination thereof.

What is claimed:

1. A gas sensor for detecting a gas in an environment, the gas sensor comprising:
   a housing having a cavity and a vent hole within the housing, wherein the cavity includes
   a bottom surface, and
   a top surface,
   wherein the housing is configured to receive the gas from the environment into the cavity through the vent hole; and
   a distributed element resonator within the cavity, wherein the distributed element resonator is configured to sense a permittivity of the gas, wherein the gas sensor has an input terminal configured to receive a radio frequency input signal and an output terminal configured to produce an output signal indicative of the permittivity of the gas.

2. The gas sensor of claim 1, wherein the distributed element resonator is a radio frequency distributed element resonator on a bottom surface of a substrate, where the bottom surface of the substrate corresponds to the bottom surface of the cavity.

3. The gas sensor of claim 2, wherein the distributed element resonator is a stub filter that includes a coupled line filter that includes an interdigitated filter, hairpin filter, or capacitive gap filter.

4. The gas sensor of claim 2, wherein the distributed element resonator is a quarter-wave stub distributed element that includes a shorted quarter-wave stub element resonator or an open quarter-wave stub element resonator.

5. The gas sensor of claim 2, wherein the distributed element resonator is a microstrip patch resonator element.

6. The gas sensor of claim 1, further comprising a heating element within the cavity, wherein the heating element is configured to heat the gas within the cavity.

7. The gas sensor of claim 6, wherein:
   the heating element is a resistive heating element patterned on the top surface of the cavity, and
   the gas sensor is configured to have a resolution of about 128 millivolts per volt.

8. The gas sensor of claim 1, wherein the cavity and the distributed element resonator are configured as a cavity resonator and the cavity is configured as a circular cavity, rectangular cavity, triangular cavity, or elliptical cavity.

9. The gas sensor of claim 1, further including an envelope detector circuit configured to generate a voltage envelope of a voltage on the output terminal.

10. A gas sensor for detecting a gas in an environment, the gas sensor comprising:
    a housing having a cavity and a vent hole within the housing, wherein the cavity includes
    a bottom surface, and
    a top surface,
    wherein the housing is configured to receive the gas from the environment into the cavity through the vent hole; and
    a distributed element resonator within the cavity, wherein the distributed element resonator has an input terminal configured to receive a radio frequency input signal and an output terminal configured to produce an output signal;
    wherein the distributed element resonator comprises a capacitor coupled between the input and output terminals and having a capacitance varying with a permittivity of the gas, the capacitor being electrically connected to the output terminal by an electrical circuit.

11. The gas sensor of claim 10, wherein the electrical circuit is configured to provide a voltage on the output terminal, the voltage being linearly proportional to the permittivity of the gas.

12. A method for fabricating the gas sensor of claim 10, the method utilizing a deposition process, the method comprising:
etching the cavity in a first substrate having a top surface and a bottom surface, wherein the cavity is etched on the bottom surface of the first substrate, and wherein the cavity has a top surface;
etching the vent hole through the top surface of the first substrate and top surface of the cavity;
depositing a first metallic layer on a second substrate, wherein the second substrate has a top surface and a bottom surface, and the first metallic layer is deposited on the top surface of the second substrate;
etching the distributed element resonator on the first metallic layer;
depositing a second metallic layer on the bottom surface of the second substrate to define a ground plane; and
bonding the bottom surface of the first substrate to the top surface of the second substrate.

13. The method of claim 12, further comprising:
etching a first via and second via through the top surface of the first substrate and the top surface of the cavity;
depositing a third metallic layer on the top surface of the first substrate and first via and the second via to define an input terminal, output terminal, and interconnects; and
depositing a fourth metallic layer within the etched cavity at the top surface of the cavity to define a heating element that is electrically connected to the interconnects.

14. The method of claim 13,
wherein the first substrate and second substrate are fabricated with silicon or glass and
wherein the first metallic layer, second metallic layer, third metallic layer, and fourth metallic layer is gold, copper, silver, or titanium.

15. The method of claim 13,
wherein the gas sensor is configured to operate in a high temperature environment,
wherein the first substrate and second substrate are fabricated with sapphire, diamond, or silicon carbide, and
wherein the first metallic layer, second metallic layer, third metallic layer, and fourth metallic layer is platinum, tungsten, or titanium.

16. A method for detecting a gas in an environment with a gas sensor, the method comprising:
receiving the gas from the environment into a cavity within a housing;
exciting a distributed element resonator within the cavity with a radio frequency input signal; and
measuring a permittivity of the gas, wherein measuring the permittivity of the gas comprises measuring an output signal from an output terminal in signal communication with the distributed element resonator, the output signal indicating the permittivity of the gas.

17. The method of claim 16, further comprising:
receiving air in the cavity prior to receiving the gas in the cavity, wherein measuring the output signal includes:
measuring a first signal profile corresponding to the air in the cavity; and
measuring a second signal profile corresponding to the gas in the cavity.

18. The method of claim 17, further comprising identifying a type of gas from measuring the output signal.

19. The method of claim 18, wherein measuring the output signal includes envelope detecting the output signal with an envelope detector.

20. The method of claim 17, further comprising:
heating the gas within the cavity;
measuring a third signal profile corresponding to the heated gas in the cavity; and
identifying a type of gas from measuring the second signal profile and the third signal profile.

* * * * *